(12) United States Patent
Gold

(10) Patent No.: US 8,753,882 B2
(45) Date of Patent: Jun. 17, 2014

(54) METHODS AND COMPOSITIONS FOR TREATING RESPIRATORY CONDITIONS USING PLATELET ENRICHED PLASMA

(75) Inventor: Richard Gold, Odessa, FL (US)

(73) Assignee: VetGel Technologies, Shrewsbury, MA (US)

( * ) Notice: Subject to any disclaimer, the term of this patent is extended or adjusted under 35 U.S.C. 154(b) by 0 days.

(21) Appl. No.: 13/272,070

(22) Filed: Oct. 12, 2011

(65) Prior Publication Data

US 2012/0087988 A1 Apr. 12, 2012

Related U.S. Application Data

(60) Provisional application No. 61/392,379, filed on Oct. 12, 2010.

(51) Int. Cl.
*C12N 15/86* (2006.01)

(52) U.S. Cl.
USPC .......................................................... 435/350

(58) Field of Classification Search
USPC .......................................................... 435/350
See application file for complete search history.

(56) References Cited

U.S. PATENT DOCUMENTS

2004/0192595 A1 9/2004 Murakami et al.
2008/0306431 A1* 12/2008 Yoo ................................. 604/20

OTHER PUBLICATIONS

Rush BR. Treatment of inflammatory airway disease: Aerosol delivery devices and medications. AAEP Proceedings. 2002;48:218-227.*
Roukis et al. Autologous platelet-rich plasma for wound and osseous healing: a review of the literature and commercially available products. Advances in Therapy. 2006;23(2):218-237.*
Heslet et al. Successful pulmonary administration of activated recombinant factor VII in diffuse alveolar hemorrhage. Critical Care. 2006;10(6):1-6.*
Daines C. What is a nebulizer, and why are inhaled medications preferred to treat asthma? Arizona Respiratory Center, Univ. of Arizona College of Medicine. 2008.*
Wang et al. Platelet rich plasma: myth or reality? European Journal of Dentistry. 2007;192-194.*
Huang et al. Potential role of platelet-derived growth factor receptor inhibition using imatinib in combination with docetaxel in the treatment of recurrent non-small cell lung cancer. J Thorac Oncol. 2011;6:372-377.*
Koc et al. Mean platelet vol. as an inflammatory marker in chronic sinusitis. Eur J Gen Med. 2011;8(4):314-317.*
USNews Health. Lung Cancer. 2009.*
University of Maryland Medical Center. Cystic fibrosis—prevention. 2011.*
National Heart, Lung and Blood Institute. How can bronchitis be prevented? 2009.*
Dr. Sneeze. Sinusitis diagnosis—prevent sinus. 2012.*
Maclay et al. Increased platelet activation in patients with stable and acute exacerbation of COPD. Thorax. 2011:66(9):769-74.*
Drew. Bleeders and lasix. 2006;1-7.*
Brown K. Hemorrhage in the broodmare. 2001;1-4.*
Johnstone et al. Hemostatic studies in racing standardbred horses with exercise-induced pulmonary hemorrhage. Hemostatic parameters at rest and after moderate exercise. Can J Vet Res. 1991;55:101-106.*
Human. Respiratory system. Ambulance technician study. 2006;1-5.*
Horses. Horses respiratory system (your horses breathing). 2009;1-2.*
Heslet et al., "Successful pulmonary administration of activated recombinant factor VII in diffuse alveolar hemorrhage," *Critical Care* 2006, vol. 10(6:R177):1-6.
International Search Report for Application No. PCT/US2011/56014, dated Feb. 23, 2012.
Written Opinion for Application No. PCT/US2011/56014, dated Feb. 23, 2012.

* cited by examiner

*Primary Examiner* — Ruth Davis
*Assistant Examiner* — Lynn Y Fan
(74) *Attorney, Agent, or Firm* — McCarter & English, LLP; Maneesh Gulati; Sanjeev K. Mahanta

(57) ABSTRACT

Described herein are methods and compositions for the treatment of respiratory diseases such as, for example, exercise induced pulmonary hemorrhage. The methods include the use of compositions comprising platelet enriched plasma, for example, platelet rich plasma and/or platelet poor plasma, for treatment of respiratory diseases in humans and animals, in particular, equines, by administration to the respiratory system.

32 Claims, No Drawings

METHODS AND COMPOSITIONS FOR TREATING RESPIRATORY CONDITIONS USING PLATELET ENRICHED PLASMA

RELATED APPLICATIONS

This application claims priority to U.S. Provisional Application No. 61/392,379, filed Oct. 12, 2010, the entire contents of which are hereby incorporated by reference herein.

TECHNICAL FIELD

Described herein are methods and compositions for the treatment of respiratory conditions of humans and animals such as equine specimens.

BACKGROUND

Horses experiencing exercise-induced pulmonary hemorrhage (EIPH), also known as "bleeding," represent a serious problem to the horse racing industry. Bleeding is a condition in which the tiny blood vessels in a horse's lungs rupture due to stress sustained during intense physical exertion. Studies of horses in training and those in competition at racetracks have shown that from about 70% to 100% of them experience EIPH after performing. This has been shown both endoscopically (Pascoe et al. 1981; Sweeney, 1991) and from transtracheal washings (Whitwell and Greet, 1984). EIPH occurs in three variations. First, there is simple EIPH which is an acute condition resulting from the strain of exercise. Second, there is patent pulmonary hemorrhage (hereinafter "PPH"), which involves bleeding in the lungs as a reaction to an allergen, infection, or due to hypertension. Third, equine specimens experience composite bleeding, which is the result of the combined effects of simple EIPH and PPH.

Although numerous hypotheses have been proffered, it is generally accepted by the scientific community that simple EIPH occurs as the natural consequence of strenuous running due to the layout of the horse's organs and the way the equine body moves during high-speed galloping. The front half of a horse contains the heart, lungs and other major organs while the posterior half contains the intestines, which are suspended within the abdomen by ligaments. The rationale is based on studies by M. Manohar (Am J. Vet. Res, 1993, 54:142-146) and West et al. (J. Appl. Physiol., 1991, 71:573-582 and J. Appl. Physiol 1993, 75: 1097-1109) among others who have demonstrated that excessive pulmonary artery pressure and stress failure at the pulmonary capillary level is due to increased transmural pressure during strenuous exercise of the equine. Due to the back-and-forth motion of galloping, the horse's intestines swing like a pendulum at the end of the ligaments. When running at full speed, especially in the fastest sprint races, the movement of the intestines can get out of phase with the movement of the diaphragm in such a way that the intestinal mass is swinging forward as the horse is trying to exhale. This causes the diaphragm to be slammed forward and slightly upward. The diaphragm, in turn, squeezes part of the lung against the chest wall.

The lungs are filled with alveoli, tiny air sacs, and capillaries, miniscule blood vessels. The alveoli and capillaries are so fine and so interconnected that oxygen from the inhaled air can pass into the bloodstream, and carbon dioxide in the blood can pass out of the blood into the lungs to be exhaled. The capillaries are at their smallest and most efficient near the rear, tapered end of the lungs where they are in close proximity to the diaphragm. These extremely fine capillaries are repeatedly impacted by the forward-surging intestinal mass. As they rupture under the stress, the horse's air passages become clogged with blood. This causes difficulty in breathing which causes reduced athletic performance and/or a shortened athletic career. Thus, EIPH is one of the most serious veterinary problems facing the horse racing industry.

EIPH is defined as bleeding from the lungs as a consequence of exertion. Most horses involved in competitive racing experience EIPH. The incidence of EIPH ranges from about 30% for standardbreds and polo ponies to greater than 60% for Thoroughbreds, Quarterhorses, Appaloosas and Arabians. The minimum level of exertion needed to induce EIPH is unknown. Though it has been observed in some Thoroughbred horses after trotting, cantering and slow training gallops, EIPH is generally associated with more strenuous exertion, such as competitive flat racing, pacing, trotting, jumping or barrel racing. Moreover, EIPH is most prevalent in Thoroughbreds.

SUMMARY OF THE INVENTION

The present invention provides methods of treating or preventing a respiratory condition in a subject suffering from or susceptible to the respiratory condition by administering at least one infusion of a composition, comprising platelet enriched plasma, including platelet-rich plasma and/or platelet poor plasma, to the lungs, for example, directly to the lungs, of the subject, thereby treating or preventing said respiratory condition. In various embodiments, the condition is selected from the group consisting of simple exercise-induced pulmonary hemorrhage (EIPH), patent pulmonary hemorrhage and a combination thereof. In a particular embodiment, the respiratory condition is simple exercise-induced pulmonary hemorrhage (EIPH) occurring in the lungs or the arteries. In other embodiments, the condition is selected from the group consisting of asthma, lung cancer, cystic fibrosis, smoke inhalation, emphysema, bronchitis, chronic obstructive pulmonary disease (COPD) and sinusitis. In a particular embodiment, the platelet enriched plasma includes platelet rich plasma (PRP). In another embodiment, the platelet enriched plasma includes platelet poor plasma (PPP). In certain embodiments, the platelet enriched plasma includes a combination of each of platelet rich plasma and platelet poor plasma.

In various embodiments, at least 2, 3, 4, 5, 6, 7, 8, 9, 10, 15 or 20 infusions of the composition are administered to the subject.

In certain embodiments, the subject is a human or an animal. In a particular embodiment, the subject is an equine, such as a stallion, mare, philly or gelding.

In various embodiments, the platelet enriched plasma may be fresh frozen plasma (FFP), autologously derived, homologously derived, or a combination thereof. Alternatively or in combination, the platelet enriched plasma comprises at least about 1%, 2%, 3%, 4%, 5%, 6%, 7%, 8%, 9%, 10%, 11%, 12%, 13%, 14%, 15% or 20% platelets. In certain embodiments, the platelet enriched plasma has a platelet concentration greater than about 200,000 platelets/$\mu$L, 300,000 platelets/$\mu$L, 400,000 platelets/$\mu$L, 500,000 platelets/$\mu$L, 600,000 platelets/$\mu$L, 700,000 platelets/$\mu$L, 800,000 platelets/$\mu$L, 900,000 platelets/$\mu$L, 1,000,000 platelets/$\mu$L, 1,100,000 platelets/$\mu$L, 1,200,000 platelets/$\mu$L, 1,300,000 platelets/$\mu$L, 1,400,000 platelets/$\mu$L, 1,500,000 platelets/$\mu$L, 1,600,000 platelets/$\mu$L, 1,700,000 platelets/$\mu$L, 1,800,000 platelets/$\mu$L, 1,900,000 platelets/$\mu$L, or 2,000,000 platelets/$\mu$L. For example, the platelet enriched plasma has a platelet concentration of greater than about 1 million platelets/$\mu$L.

In other embodiments, the composition comprises at least 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175 or 200 mL of platelet enriched plasma.

The administration of platelet enriched plasma may enhance platelet concentration in the subject by at least 1, 2, 3, 4, 5, 6, 7, 8, 9 or 10 times. Alternatively or in addition, the administration of platelet enriched plasma enhances concentration of at least one growth factor in the subject by at least 1, 2, 3, 4, 5, 6, 7, 8, 9 or 10 times. For example, the at least one growth factor is selected from the group consisting of transforming growth factor beta (TGFbeta), vascular endothelial growth factor (VEGF), platelet-derived growth factor (PDGF), epidermal growth factor (EGF) and epithelial growth factor (EDF).

In one embodiment, the composition is administered directly to at least one lung. In an alternative embodiment, the composition is administered directly to the respiratory system upstream of the lungs and is subsequently transmitted to the lungs. For example, the composition may be administered directly to the bronchia, nasal cavity, sinuses, mouth, larynx, trachea or carina. In a particular embodiment, the composition is administered into at least one lung by direct administration to the carina, whereby the composition is subsequently transmitted to the main bronchi of at least one lung of the subject.

In certain embodiments, the composition is administered to the subject through an endoscopic biopsy channel, by use of a nebulizer, or through a syringe.

In various embodiments, the methods includes administering to the subject at least one of a platelet trigger or a diuretic, for example, furosemide. For example, the platelet trigger or diuretic, for example, furosemide, is administered previously, subsequently, or substantially simultaneously to the administration of the platelet enriched plasma. In certain embodiments, the composition includes at least one of the platelet trigger or the diuretic, for example, furosemide. The administration of platelet enriched plasma and platelet trigger in these foregoing embodiments may result in the release of at least one growth factor by platelet alpha granules, for example, transforming growth factor beta (TGFbeta), vascular endothelial growth factor (VEGF), platelet-derived growth factor (PDGF), epidermal growth factor (EGF) and epithelial growth factor (EDF). In a particular embodiment, the growth factor is TGFbeta.

In a further aspect, the invention is directed to a kit including a composition of platelet enriched plasma and instructions for administering the composition to the lungs of the subject. The platelet enriched plasma may be either autologous or homologous. The platelet enriched plasma may include platelet rich plasma, platelet poor plasma, or a combination thereof.

In certain embodiments, the kit may further include a means for administering the platelet enriched plasma to at least one lung of the subject, for example, an endoscopic biopsy channel, a syringe or a nebulizer. In certain embodiments, the means for administering the platelet enriched plasma to at least one lung of the subject is a means for directly administering the platelet enriched plasma to the at least one lung of the subject. Alternatively, the means for administering the platelet enriched plasma to at least one lung of the subject is a means for directly administering the platelet enriched plasma to the respiratory system upstream of the lungs, which is subsequently transmitted to the lungs. For example, the platelet enriched plasma may be administered direct to the bronchia, nasal cavity, sinuses, mouth, larynx, trachea or carina.

In certain embodiments, the kit may further include a platelet trigger and/or a diuretic, for example, furosemide.

In a further aspect, the present invention is directed to a method of treating or preventing exercise induced pulmonary hemorrhage in an equine by administering to the lung of the equine, a composition including platelet enriched plasma, wherein the composition is infused at the level of the carina such that it is distributed to the main bronchi of at least one lung of the equine, thereby treating or preventing exercise induced pulmonary hemorrhage.

The present invention is further illustrated by the following detailed description.

DETAILED DESCRIPTION

The present invention is based, at least in part, on the unexpected finding that the administration of compositions including platelet enriched plasma, to the respiratory system, can serve to treat or prevent respiratory conditions, in particular, simple exercise induced pulmonary hemorrhage (EIPH) or other respiratory conditions characterized by respiratory bleeding. Without wishing to be bound by any particular theory, platelet enriched plasma may serve to (1) repair damaged endothelial lining of blood vessels in the lung associated with EIPH; (2) promote vasculogenesis and angiogenesis as collateral means of circulation after injury to existing vessels; and/or (3) promote local immunity and healing of tissue damaged by biofilm (i.e., bacteria and other microorganisms) infection in lungs.

As used herein, each of the following terms has the meaning associated with it in this section.

The articles "a" and "an" are used herein to refer to one or to more than one (i.e., to at least one) of the grammatical object of the article.

The term "administering" includes any method of delivery of the therapeutic compositions of the present invention into a subject's system or to a particular region in or on a subject. Preferably, the compositions are administered to the respiratory system as described herein. Furthermore, as used herein, the term "infusion" refers to a single administration to the body of a subject of a composition as described herein.

The term "subject" as used herein, refers to animals, including humans, to be administered the compositions and/or treated by the methods of the present invention. A subject includes an animal that is suffering from, at risk to suffer from or suspected of suffering from a respiratory condition, for example, a respiratory condition associated with respiratory bleeding. A subject also includes animals to be treated so as to prevent undesired respiratory conditions. Furthermore, a subject includes animals having an ineffective ability to naturally curb respiratory bleeding. Subjects include animals (e.g., humans, wild animals and domesticated animals such as cats, dogs, goats, cows, pigs and chickens). In one embodiment, the subject is an animal that is involved in competitive sport, for example, competitive racing, including, but not limited to, horses and dogs.

As used herein, the terms "treating" or "treatment" refer to a beneficial or desired clinical result including, but not limited to, alleviation or amelioration of one or more symptoms of the respiratory condition; diminishing the extent of the respiratory condition, e.g., respiratory bleeding; stabilized (i.e., not worsening) state of the respiratory condition, e.g., respiratory bleeding; amelioration or palliation of the respiratory condition, e.g., respiratory bleeding; and remission (whether partial or total), whether detectable or undetectable. "Treatment" can also mean prolonging survival as compared to expected survival in the absence of treatment.

As used herein, the term "respiratory condition" refers to a disruption of normal respiratory function and/or activity of tissues, organs, and cells of the respiratory system (e.g., nose, ears, sinuses, throat, trachea, bronchial tubes, and lungs) caused by or associated with an environmental factor, irritant, an infectious agent and/or physical damage. Respiratory conditions induced by environmental irritants include, but are not limited to, asthma and allergies. Symptoms of a respiratory condition include, but are not limited to, increased mucus production, coughing, bronchoconstriction (i.e., wheezing), fever, sinus pain, lesions in the lung, inflammation of bronchial tubes, sore throat, and/or elevated IgE levels. Respiratory conditions induced by physical damage include respiratory bleeding. In addition, respiratory conditions include, but are not limited to simple exercise-induced pulmonary hemorrhage (EIPH), patent pulmonary hemorrhage and a combination thereof, asthma, lung cancer, cystic fibrosis, smoke inhalation, emphysema, bronchitis, chronic obstructive pulmonary disease (COPD) and sinusitis.

As used herein, the terms "bleeding" and "EIPH" are used interchangeably to refer to exercise induced pulmonary hemorrhage. As used herein, EIPH includes simple EIPH, PPH and composite bleeding. Simple EIPH is an acute condition resulting from the strain of exercise. Patent pulmonary hemorrhage (hereinafter "PPH") involves bleeding in the lungs as a reaction to an allergen, infection, or due to hypertension. Composite bleeding refers to a condition arising from the combined effects of simple EIPH and PPH.

As used herein, the term "breeze" is used interchangeably with the term "work" and refers to running a horse, preferably under a hold and with minimal encouragement.

As used herein, the term "platelet enriched plasma" refers to a plasma composition having a concentration of platelets above that of the concentration of platelets normally found in blood. In a particular embodiment, platelet concentration is above the normal baseline concentration of platelets, for example, about 200,000 platelets/μL. For example, the platelet concentration may be at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, 45, 50, 55, 60, 65, 70, 75, 80, 85, 90, 95, or 100 times or more the normal concentration in blood. In certain embodiments, the platelet enriched plasma has a platelet concentration greater than about 200,000 platelets/μL, 300,000 platelets/μL, 400,000 platelets/μL, 500,000 platelets/μL, 600,000 platelets/μL, 700,000 platelets/μL, 800,000 platelets/μL, 900,000 platelets/μL, 1,000,000 platelets/μL, 1,100,000 platelets/μL, 1,200,000 platelets/μL, 1,300,000 platelets/μL, 1,400,000 platelets/μL, 1,500,000 platelets/μL, 1,600,000 platelets/μL, 1,700,000 platelets/μL, 1,800,000 platelets/μL, 1,900,000 platelets/μL, or 2,000,000 platelets/μL. Alternatively or in combination, the "platelet enriched plasma" comprises at least about 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90% or 95% platelets. In some embodiments, the "platelet enriched plasma" contains about 6.5% platelets. In other embodiments, the "platelet enriched plasma" contains at least 6.5% platelets.

As used herein, the term "platelet enriched plasma" includes both "platelet rich plasma" and "platelet poor plasma," each of which are known in the art to have a concentration of platelets above that of the concentration of platelets normally found in blood. While platelet rich plasma is known to have a concentration of platelets higher than that of platelet poor plasma, each is known to have a concentration of platelets greater than the normal concentration of platelets in whole blood. Each of platelet rich plasma and platelet poor plasma can be obtained by centrifugation of whole blood. Upon centrifuging whole blood and removal of the solid precipitate, a tiered plasma composition remains. The lower plasma tier constitutes a highly enriched plasma composition, i.e., platelet rich plasma. The higher plasma tier constitutes a less enriched plasma composition, i.e., platelet poor plasma.

In a particular embodiment, the platelet enriched plasma, for example, platelet rich plasma and/or platelet poor plasma, may use the subject's own plasma as the carrier. The platelet enriched plasma may be formed from whole blood, e.g., by technology disclosed in any of U.S. Pat. Nos. 5,614,106; 5,580,465; 5,258,126 or publication cited in these patents and, if necessary, stored by technology as taught in U.S. Publication No. 2002/0034722A1; U.S. Pat. No. 5,622,867 or publications cited therein. The platelet enriched plasma may comprise blood component other than platelets. The non-platelet components may be plasma, white blood cells and/or any blood component. According to the present invention, platelet enriched plasma can be formed from the concentration of platelets from whole blood. In addition, in certain embodiments, platelet enriched plasma may be formed from a variety of animal sources, including human and equine sources. Additionally, the platelet enriched plasma may be obtained using autologous, allogenic, or pooled sources of platelets and/or plasma. In a particular embodiment, the platelet enriched plasma is autologous or, alternatively, homologous. Alternatively, the platelet enriched plasma may be a combination of homologous and autologous.

In various embodiments, the compositions of the present invention may consist exclusively of platelet enriched plasma (e.g., platelet rich plasma and/or platelet poor plasma). Alternatively, the compositions may consist essentially of platelet enriched plasma (e.g., platelet rich plasma and/or platelet poor plasma). Finally, the compositions may include platelet enriched plasma (e.g., platelet rich plasma and/or platelet poor plasma) or other elements as described herein.

As used herein, the term "modulate" or "modulated" refers to the reduction or elimination of the treated respiratory condition.

As used herein, the term "autologous" refers to blood donation wherein the donor and recipient are the same.

As used herein, the term "homologous" refers blood donation wherein the donor and recipient are different.

The present invention includes methods for treating various respiratory conditions in subjects. In particular, the present invention provides methods for treating EIPH and other conditions related to respiratory bleeding. As described above, EIPH has several forms including simple EIPH, PPH or a combination of the two. Provided herein are methods of modulating these conditions and conditions related to them by administering to a subject in need thereof, a composition including platelet enriched plasma (e.g., platelet rich plasma and/or platelet poor plasma).

Composition

In some embodiments of the invention, a subject suffering from, or susceptible to, a respiratory condition such as respiratory bleeding (i.e. EIPH, PPH or a combination) is treated with a composition containing platelet enriched plasma (e.g., platelet rich plasma and/or platelet poor plasma).

Blood is made up of many components including red blood cells, white blood cells, platelets, plasma, clotting factors, and small proteins. Each component has a different metabolic responsibility. Red blood cells help pick up oxygen from the lungs and deliver it to the other body cells while removing carbon dioxide. White blood cells fight infections, kill germs, and carry off dead blood cells. Plasma, in part, contains clotting factors that help blood to clot, for example, by capturing platelets. For example, the clotting factor fibrinogen present in plasma catches platelets at a wound site to help form clots. Captured platelets are responsible for hemostasis, construction of new connective tissue and revascularization, each of which are important functions to counteract the effects of respiratory conditions, such as EIPH.

Typically, a blood specimen contains 43% red blood cells (hereinafter "RBC"), 6% platelets, 1% white blood cells and 50% plasma (hereinafter "WBC"). Indeed, a unit of blood (i.e., 1 pint of blood) contains only a small volume of platelets. Accordingly, it often takes several units of platelets, defined as the amount of platelets that can be separated from a unit of whole blood, to stop bleeding in a subject.

In accordance with the methods of the present invention, whole blood may be separated into its components, including RBCs, plasma, platelets, and/or cryoprecipitate, for example, by centrifugation and separation through a batch process. Specifically, the blood may be spun for a period of about 10 minutes in a large refrigerated centrifuge. The main blood constituents, i.e., red blood cells, platelets, white blood cells, and plasma, having sedimented and formed distinct layers, can then be expressed sequentially by a manual extractor in multiple satellite bags attached to the primary bag. As taught above, upon centrifuging whole blood and removal of the solid precipitate, a layered plasma composition remains where the lower plasma layer constitutes a highly enriched plasma composition, i.e., platelet rich plasma, and the higher plasma layer constitutes a less enriched plasma composition, i.e., platelet poor plasma.

Related systems for separating blood components for use in the present invention are described in U.S. Pat. Nos. 4,387,848; 4,094,461; 4,007,871; 4,010,894, 5,316,540 and 6,942,639, which are herein incorporated by reference in their entirety. One of ordinary skill in the art would understand that other equivalent means are also contemplated. For example, apheresis methods of separating blood may be employed. Certain apheresis processes include attaching the donor to a machine that removes blood, then separating the plasma into a different container. The machine then returns the red blood cells and other parts of the blood back to the donor's blood stream. Once plasma is separated from the other components, it can be frozen and kept for up to a year until it is needed. Once thawed, it is called fresh frozen plasma (FFP).

Platelets can also be collected by apheresis which is sometimes called plateletpheresis. In this procedure a donor is hooked up to a machine that removes the blood, and retains just the platelets. The rest of the blood cells are returned to the donor. Apheresis can collect enough platelets so that the platelets do not have to be pooled with platelets from other donors, although such supplementation may be employed in other embodiments of the invention.

As taught herein, in various embodiments, the platelets from the platelet enriched plasma compositions of the present invention are activated to release growth factors, which, in turn, accelerate tissue and wound healing. Therefore, the administration of the compositions of the present invention serve to increase the systemic concentration of growth factors, thereby contributing to the healing and treatment of respiratory conditions. Alternatively or in combination, growth factors may be incorporated within the compositions of the invention and/or may be administered prior to, following or simultaneously with the administration of the compositions of the invention to substantially enhance tissue and cell recovery such as those that cause EIPH.

The present invention provides methods wherein plasma and platelets are separated from other components such that the plasma is highly concentrated above baseline with platelets. The platelets having the ability to release the growth factors necessary for healing are administered to the subject in a composition comprising platelet enriched plasma.

The platelets contain alpha granules which contain the clotting and growth factors that are eventually released in the healing process. Normally at the resting state, platelets require a trigger to activate and become participants in wound healing and hemostasis. In some embodiments of the present invention, the platelets are activated to release the clotting and growth factors. In certain embodiments, a suitable trigger is included in the composition or is simultaneously or subsequently administered to the subject such that the clotting and growth factors, needed for modulation of EIPH, are released. While one of ordinary skill in the art may contemplate many equivalent triggers, thrombin is a suitable trigger for activating the platelets and morphing them into pseudo-pods that spread over injured tissue. Suitable triggers cause the alpha granules in the platelets to release the growth factors, which stimulate inflammatory cascade and healing.

Growth factors for use with the methods of the present invention include, but are not limited to, transforming growth factor beta (TGFbeta), vascular endothelial growth factor (VEGF), platelet-derived growth factor (PDGF), epidermal growth factor (EGF) and epithelial growth factor (EDF). TGFbeta is active during inflammation and influences the regulation of cellular migration and proliferation, the stimulation of cell replication, and fibronectin binding interactions. VEGF is produced at its highest levels only after the inflammatory phase, and is a potent stimulator of angiogenesis. Angiogenesis, regulation of cellular proliferation, replication, and fibronectin binding interactions are important factors in modulating EIPH. Accordingly, the present invention, in some aspects, includes the use of platelet enriched plasma to modulate these factors in treating EIPH and other respiratory conditions related to bleeding.

Subjects

As described above, the present invention contemplates treatment of subjects suffering from or susceptible to a condition related to respiratory bleeding whereby the subject is administered, to the respiratory system, a composition containing platelet enriched plasma (e.g., platelet rich plasma and/or platelet poor plasma) such that the condition is modulated.

The term "subject" as used herein, refers to animals, including humans, to be administered the compositions and/or treated by the methods of the present invention. A subject includes an animal that is suffering from, at risk to suffer from or suspected of suffering from a respiratory condition, for example, a respiratory condition associated with respiratory bleeding. A subject also includes animals to be treated so as to prevent undesired respiratory conditions. Furthermore, a subject includes animals having an ineffective ability to naturally curb respiratory bleeding. Subjects include animals (e.g., humans, wild animals and domesticated animals such as cats, dogs, goats, cows, pigs, chickens, bovine, equine, canine and feline). In one embodiment, the subject is an animal that is involved in competitive sport, for example, competitive racing, including, but not limited to, horses and dogs. In another embodiment, the subject is a human.

Equine specimens are particularly susceptible to respiratory bleeding due to their body structure and the stress endured by the lungs during exercise or horse racing. As discussed herein, due to the layout of the body and organs of an equine specimen, the fine capillaries in the rear of the lung are repeatedly impacted by the forward surging intestinal mass during running. As they rupture under the stress, the horse's air passages become clogged with blood. This causes difficulty in breathing which causes reduced athletic performance and/or a shortened athletic career. For instance, Thoroughbred race horses commonly exhibit respiratory bleeding which reduces racing performance and produces other health complications. Equine specimens may also suffer from PPH, which is bleeding in the lungs as a reaction to an allergen, infection, or due to hypertension. Other equine specimens may suffer from both simple EIPH and PPH.

In some embodiments of the present invention, the equine specimen may be a Thoroughbred, Quarterhorse, standardbred, Arabian, steeplechaser, heavy draft horse or Appaloosa. In certain embodiments, the equine may also be a stallion, mare, philly or gelding.

Accordingly, the present invention provides methods of treating respiratory conditions, for example, EIPH, in equine specimens by direct administration of platelet enriched plasma (e.g., platelet rich plasma and/or platelet poor plasma) to the respiratory system of the equine. Accordingly, in certain embodiments, the methods of the present invention serve to treat horses suffering from respiratory bleeding often stemming from the rupture of tiny blood vessels in a horse's lungs sustained during physical exertion. Indeed, in many horses, the respiratory bleeding is attributed to exercise related stress or, alternatively, it may be in reaction to allergens.

The bleeding may be in the lungs, bronchi, alveoli, nasal cavity, sinuses, mouth, larynx, trachea, arteries or carina of the subject. Accordingly, in various embodiments of the invention, the compositions of the invention are administered to the respiratory system so as to treat or prevent bleeding in the lungs, bronchi, alveoli, nasal cavity, sinuses, mouth, larynx, trachea, arteries or carina of the subject. For example, the compositions of the invention, including platelet enriched plasma, may be administered to the nasal cavity, sinuses or mouth of a subject so as to treat or prevent bleeding in the bronchi of the subject.

The present invention provides methods for treating a subject suffering from EIPH by administering a first infusion of the platelet enriched plasma described herein, into the respiratory system of the equine specimen. In some embodiments, the subject may be administered at least one further infusion of the platelet enriched plasma.

Administration

Presented herein are methods of treating a subject suffering from or susceptible to a respiratory condition and, in particular, a condition related to respiratory bleeding. In preferred embodiments of the invention, the methods include administering an infusion of platelet enriched plasma into the respiratory system of the subject.

Disclosed herein are methods of modulating the bleeding caused by EIPH, PPH or both. In certain embodiments, a subject, human or animal is administered a first infusion of a composition comprising platelet enriched plasma. The composition in its entirety or the platelet enriched plasma by itself may be administered to the subject by direct administration to the respiratory system so as to substantially modulate the condition related to the respiratory bleeding. In certain embodiments, the composition, including the platelet enriched plasma or the platelet enriched plasma by itself, is administered to, for example, directly into, the lung, bronchi, alveoli, nasal cavity, nostrils, sinuses, mouth, larynx, trachea or carina of the subject so as to allow transport of the platelet enriched plasma to the lungs. Preferably, the platelet enriched plasma is injected or otherwise administered into the lung. In certain embodiments, the platelet enriched plasma is injected or otherwise administered to the carina so as to have the platelet enriched plasma distributed to the main bronchi of at least one lung, preferably both lungs.

In certain embodiments, methods are provided for the treatment of EIPH in a racehorse. A composition containing a combined 35 mls of platelet-rich plasma and platelet poor plasma is infused at the level of the carina such that it is distributed to the main bronchi of each lung of the racehorse, such that the EIPH is at least substantially reduced. In some embodiments the EIPH is completely alleviated such that the bleeding is stopped.

In other embodiments, the racehorse suffering from or susceptible to EIPH is administered multiple infusions of platelet-rich plasma over a period 1, 2, 3, 4, 5, 6, 7, 8, 9, 10, 11, 12, 13, 14, 15, 16, 17, 18, 19 or 20 days.

In certain embodiments, the tubing of an endoscopy aspiration kit, that is fed through the channel, is used to administer the infusion of the platelet enriched plasma to the subject. In other embodiments, an endoscopic biopsy channel is used to infuse the plasma into the lungs or neighboring tissue.

In other embodiments, the platelet enriched plasma is administered by use of a nebulizer. For example, in certain embodiments, platelet enriched plasma is administered to the lungs in the form of mist generated by a nebulizer.

EXAMPLES

The invention will be further understood by the following example(s). However, those skilled in the art will readily appreciate that the specific experimental details are only illustrative and are not meant to limit the invention as described herein, which is defined by the claims which follow thereafter.

Example 1

Platelet Rich Plasma for Use In Treatment of Exercise Induced Pulmonary Hemorrhage After endoscopically examining a four year old gelding, it was observed that the gelding displayed evidence of significant bleeding. After his poorest race performance to date, a grade 8 (on a one to ten scale, with ten being severe bleeding from both nostrils) pulmonary hemorrhage was determined. The gelding had been treated with 350 mg of Furosemide® intravenously prior to the race. He had no lameness problems, no other respiratory abnormalities and also remained with the same trainer throughout the therapeutic treatments. Training schedule and exercise protocols were not dramatically altered. After treatment with platelet-rich plasma therapy administered directly into his lungs, his racing performance continually improved. He suffered no side effects after his two treatments and actually seemed healthier and more energetic. The gelding rebounded from each subsequent race, better than the previous, and showed continual improvement with a significant reduction of pulmonary hemorrhage. Medications prior to race-day and on race-day were kept consistent.

Approximately 35 ml of combined infusion of platelet-rich plasma (PRP) and platelet poor plasma (PPP) were administered directly to the lung of the gelding. 8 days later, a second infusion with the same methodology and product was administered to the gelding. 5 days later, the gelding was treated with 400 mg furosemide prior to racing and displayed no bleeding. Approximately one month following the initial combined infusion, the gelding was treated with 400 mg of furosemide prior to racing and displayed a few streaks of blood. Two weeks later, the gelding was treated with 400 mg of furosemide prior to racing and displayed no bleeding. Approximately three weeks later, the gelding was treated with 400 mg of furosemide prior to racing and displayed a grade 2 bleeding. Approximately 2 weeks later, the gelding trained for a half mile breeze and was treated with 400 mg of furosemide prior to training and displayed a grade 3 bleeding. Finally, a week later, the gelding was treated with 400 mg of furosemide prior to racing but no scope was performed, as the gelding had won the event.

Example 2

Kit and Instructions for Generating and Administering Platelet Rich Plasma

A kit for generating and administering platelet rich plasma was assembled. The kit included, in part, syringes, an aspiration kit, sterile water, scissors, Anticoagulant Citrate Dextrose solution, needles, cannulas and other containers. Instructions for use of the kit and generating platelet rich plasma are as follows:

Place process disposable (white plastic cup) in centrifuge and align up white injection port with the white dot. These instructions require a single blue balance weight (BW-60), except when using two process disposables with blood from the same horse, which requires no balance weight. Tighten down the two cannulas and close plungers on the 20 ml and 30 ml syringes (remove and discard the two yellow spacers on the 30 ml syringe). After removing the spacers, replace the plastic shield on 30 ml syringe to maintain sterility.

Insert 2 ml of Anticoagulant Citrate Dextrose (ACD) Solution in a 3 ml syringe (using the red blunt fill needle) and, subsequently, inject through the white injection port on the process disposable.

Insert 6 ml of ACD in 60 ml syringe using the red blunt fill needle. Remove and discard the red blunt fill needle and add doctor's preferred needle for phlebotomy. Withdraw blood exactly to 60 ml. The composition should consist of 6 ml ACD and 54 ml blood.

Replace phlebotomy needle with enclosed blunt plastic cannula and slowly inject 60 ml blood through red injection port. Note: Be sure cannula tip is straight-up (perpendicular) and is in the center of the injection port. Entering off-center or applying excessive pressure on red injection port may dislodge it into the process disposable, thus rendering it useless and requiring the use of a new kit.

Close lid of centrifuge (amber "LID OPEN" light must be off). Press green button to start 14 minute spin. Note: Process of preparing final product should be completed within two hours of completing this step to avoid degradation of platelet rich plasma and growth factors.

At this point (after re-suspension of platelet and growth factor concentrate), approximately 40 ml of Platelet Rich Plasma (PRP) will remain. Insert the long silver blunt cannula with 30 ml syringe through the white injection port into the platelet and growth factor concentrate layer (visible reddish layer) without going through the platelet and growth factor concentrate layer (buffy coat). Slowly withdraw 30 ml of 40 ml amount of platelet enriched plasma into a syringe. Without removing the cannula from the process disposable, tilt the syringe, and gently squirt the entire amount against one side of the process disposable, then slowly withdraw 30 ml of the remaining 40 ml back into the syringe. Repeat the above mentioned step two times to the opposite sides of process disposable. (Note: Additional mixing of platelet and growth factor concentrate layer with plasma adds no additional benefit). Do not remove the cannula from the process disposable.

Using the long silver blunt cannula (already in the process disposable), remove 20 ml of reddish-tinged platelet rich plasma. Then remove the 30 ml syringe and set aside for injection into the platelet rich plasma delivery kit.

Attach the long silver blunt cannula to the 20 ml syringe and insert into the white injection port to remove the remaining reddish-tinged final product (approximately 16-20 ml of platelet rich plasma) for injection into delivery kit.

Instructions for delivering platelet rich plasma are as follows:

Antiseptic protocol is extremely important considering the direct application into both lungs. Clean the external nares of the intended endoscope insertion.

Using one of the two remaining 60 ml syringes (without any needle), withdraw 50 ml of enzymatic/disinfectant solution and flush the entire amount into an endoscopic channel. Using the other 60 ml syringe (with the red blunt fill needle), withdraw 50 ml of sterile water, then remove the needle and flush the entire amount into an endoscopic channel.

Place tubing of platelet rich plasma delivery kit through the endoscopic channel and extend tubing 4 inches past the distal tip. Using the sterile scissors, cut and discard 4 inches of tubing from the distal end of the endoscope, thereby eliminating and ensuring against possible contamination during endoscopic placement.

Retract tubing back into the endoscope to protect from possible contamination on passage of endoscope.

Introduce the endoscope into the cleaned nares and place as distal as possible to the carina or major left or right bronchi. Advance the tubing past the distal end of the endoscope towards the visual opening. Administer the approximate 20 ml of platelet rich plasma directly into the left or right lung (via the left or right bronchi). Using the 20 ml syringe of final product, repeat in order to administer the remaining approximate 16-18 ml of platelet rich plasma into the opposite bronchi.

After completion, using the same syringe, inject 15 ml of air to completely remove the remaining platelet rich plasma from the delivery kit.

Example 3

Protocol for Treatment of EIPH by Administration of Platelet Rich Plasma

A recommended protocol for treatment of EIPH by administration of platelet rich plasma was generated as follows:

Determine whether the horse suffers from EIPH via endoscopic examination.

Treat or prevent potential infections by administration of antibiotics in horses with severe bleeding.

Institute treatment with a bronchodilator, and maintain throughout initial treatment "quiet" period (3 weeks). Use afterwards as desired by veterinarian and trainer.

During quiet three week period following initial diagnostic endoscopic examination, permitted training protocol is limited to jogging and galloping only. No fast strenuous training is permitted.

Perform first platelet rich plasma (PRP) treatment, for example, as set forth in Examples 2 and 3, three weeks after the initial bleed.

Nine days after the initial PRP treatment, perform a second PRP treatment. During this time, "breezing" between plasma treatments is acceptable, but at no distance greater than ½ mile.

Racing after one week from the second plasma treatment is acceptable. The horse should be "walked" into the initial race for the four days prior to the race.

Treatment results have been best when the horse is alternatively jogged and galloped as a general training protocol after plasma treatments have been completed. When the horse needs to be trained faster and longer for fitness, walk the horse for two days and then incorporate a slow gallop of 1½ miles and "works" of no greater than ½ mile and a strong "gallop out". Preferably do not breeze the horse more than one breeze per week. Appropriate "bleeder" medication for any "works" must be incorporated as for treating any suspected severe bleeder. Prior to racing (after the first race), galloping into the race, for the three to four days is recommended.

Example 4

Platelet Rich Plasma for Use In Treatment of Exercise Induced Pulmonary Hemorrhage A veterinarian reported administration of 10 horses identified as suffering from Exercise Induced Pulmonary Hemorrhage (EIPH) with platelet rich plasma (PRP). The veterinarian reported that the administration of PRP resulted in reducing the amount of bleeding upon post-exercise endoscopic examination. In particular, the veterinarian reported that one horse suffered from bleeding in both nostrils after a race in which the horse performed poorly. The horse underwent two PRP treatments about 10 days apart. The horse had "a much improved racing performance" in a subsequent race and exhibited "only a minimal amount of blood in the tracheas."

Another veterinarian reported the results of PRP treatment in several race horses who had exhibited bleeding.

1) A 3 year old filly had bled at a grade 8 (on a one to ten scale, with ten being severe bleeding from both nostrils) during two races. The horse was considered for retirement from racing. The horse received PRP treatment. 10 days later, the horse was worked, i.e., breezed, but exhibited no bleeding. 8 days later, the horse was worked again, but again exhibited no bleeding. The horse received a second PRP treatment. A week later, the horse participated in a race and bled at a grade 8 and finished last. The horse was raced again two weeks later and bled at a grade 1 and finished $3^{rd}$.

2) A 4 year old gelding was characterized as a "bad bleeder". The horse received initial PRP treatment. Two weeks later, the horse was worked and bled at a grade 2. The horse received a second PRP treatment. A week later, the horse was worked again and bled at a grade 2.

3) A 9 year old gelding experienced bleeding out of both nostrils when at gallop. The horse received three PRP treatments but continued to exhibit bleeding from one or both nostrils. The horse was retired from racing.

4) A 5 year old filly experienced bleeding out of both nostrils following a race. The filly underwent PRP treatment. Two weeks later, the horse was worked and exhibited a grade 0. The horse received a second PRP treatment approximately 10 days later and during subsequent exercise, exhibited a grade 0.

5) A 4 year old filly experienced bleeding at a grade 8 following a race. The horse underwent two PRP treatments nearly 3 weeks apart. 2 weeks after the second PRP treatment, the horse was worked and exhibited a grade 0.

Another veterinarian reported the results of PRP treatment in several race horses who had exhibited bleeding. Each of these horses received the following PRP treatment. Treatment protocol included two weeks of rest after experiencing a severe bleed. The horses subsequently received two PRP infusions ten days apart, followed by a two week "quiet" period with no significant working. After each PRP treatment, the horses received at least one full day off and were only walked. No medical problems were reported post infusion for any of the horses.

1) A horse had experienced "trickling" of blood from the nostrils after prior racing. The horse was administered platelet enriched plasma. The horse finished $1^{st}$ and $2^{nd}$ at subsequent races having received 400 mgs of furosemide prior to racing. A scope exam revealed improved results with respect to bleeding, exhibiting bleeding at grade 3.

2) A horse had experienced "severe, profuse, out the nose" bleeding. The horse was administered platelet enriched plasma after two months of rest. The horse finished $2^{nd}$, $4^{th}$ and $6^{th}$ at subsequent races having received 300 mgs of furosemide prior to racing. Scope exams revealed substantially improved results with respect to bleeding. Scope exams revealed bleeding ranging from one spot of blood to bleeding at grade 2.

3) A filly had experienced bleeding from the nostrils upon competitive racing. The filly was treated twice with platelet enriched plasma. Following treatment, the trainer learned that the filly had suffered from severe respiratory disease as a very young horse and had likely suffered permanent lung damage preventing future competitive racing.

4) A horse had experienced bleeding after a competitive race. The horse was subsequently administered platelet enriched plasma. She was subsequently worked after being administered 350 mg of furosemide. Subsequent scoping revealed no bleeding.

The present invention provides novel therapy for respiratory conditions related to respiratory bleeding. Both equine and human, suffering from EIPH or COPD, asthma, cancer or other respiratory ailments may benefit from the platelet enriched plasma therapy disclosed herein by directly administering the platelet enriched plasma to the respiratory system of the subject, especially to the lung, carina, alveoli, trachea, nasal cavity, sinuses, mouth, larynx or bronchi.

Those skilled in the art will recognize, or be able to ascertain using no more than routine experimentation, many equivalents to the specific embodiments of the invention described herein. Such equivalents are intended to be encompassed by the following claims.

All publications and patent documents cited in this application are incorporated by reference in pertinent part for all purposes to the same extent as if each individual publication or patent document were individually denoted. By their citation of various references in this document, Applicants do not admit any particular reference is "prior art" to their disclosure. It is to be understood that while the present disclosure has been described in conjunction with the detailed description thereof, the foregoing description is intended to illustrate and not limit the scope of the present disclosure, which is defined by the scope of the appended claims. Other aspects, advantages, and modification are within the scope of the following claims and their equivalents.

While specific examples have been provided, the descriptions are illustrative and not restrictive. Any one or more of the features of the previously described embodiments can be combined in any manner with one or more features of any other embodiments in the present disclosure. Furthermore, many variations of the present disclosure will become apparent to those skilled in the art upon review of this disclosure.

The invention claimed is:

1. A method of treating a respiratory condition in an equine suffering from said respiratory condition comprising administering at least one infusion of a composition comprising autologous platelet enriched plasma to at least one lung of the equine, thereby treating said respiratory condition, wherein said respiratory condition is pulmonary hemorrhage.

2. The method of claim 1, wherein the condition is patent pulmonary hemorrhage.

3. The method of claim 1, wherein the respiratory condition is simple exercise-induced pulmonary hemorrhage (EIPH).

4. The method of claim 3, wherein the EIPH occurs in the lungs or the arteries.

5. The method of claim 1, wherein the platelet enriched plasma comprises platelet rich plasma (PRP).

6. The method of claim 1, wherein the platelet enriched plasma comprises platelet poor plasma (PPP).

7. The method of claim 1, wherein the platelet enriched plasma comprises each of platelet rich plasma and platelet poor plasma.

8. The method of claim 1, wherein at least 2, 3, 4, 5, 6, 7, 8, 9, 10, 15 or 20 infusions of the composition are administered to the equine.

9. The method of claim 1, wherein the equine is a stallion, mare, filly or gelding.

10. The method of claim 1, wherein the platelet enriched plasma is fresh frozen plasma (FFP).

11. The method of claim 1, wherein the platelet enriched plasma is autologous platelet concentrate (APC).

12. The method of claim 1, wherein the platelet enriched plasma comprises at least about 1%, 2%, 3%, 4%, 5%, 6%, 7%, 8%, 9%, 10%, 11%, 12%, 13%, 14%, 15%, 16%, 17%, 18%, 19% or 20% platelets.

13. The method of claim 1, wherein the platelet enriched plasma has a platelet concentration greater than about 100,000 platelets/µL, 200,000 platelets/µL, 300,000 platelets/µL, 400,000 platelets/µL, 500,000 platelets/µL, 600,000 platelets/µL, 700,000 platelets/µL, 800,000 platelets/µL, 900,000 platelets/µL or 1,000,000 platelets/µL.

14. The method of claim 1, wherein the platelet enriched plasma has a platelet concentration of greater than about 1 million platelets/µL.

15. The method of claim 1, wherein the composition comprises at least 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175 or 200 mL of platelet enriched plasma.

16. The method of claim 1, wherein the administration of platelet enriched plasma enhances platelet concentration in the equine by at least 1, 2, 3, 4, 5, 6, 7, 8, 9 or 10 times.

17. The method of claim 1, wherein the administration of platelet enriched plasma enhances concentration of at least one growth factor in the subject by at least 1, 2, 3, 4, 5, 6, 7, 8, 9 or 10 times.

18. The method of claim 17, wherein the at least one growth factor is selected from the group consisting of transforming growth factor beta (TGFbeta), vascular endothelial growth factor (VEGF), platelet-derived growth factor (PDGF), epidermal growth factor (EGF) and epithelial growth factor (EDF).

19. The method of claim 1, wherein the composition is administered directly to at least one lung.

20. The method of claim 1, wherein the composition is administered directly to the respiratory system upstream of the lungs and is subsequently transmitted to the lungs.

21. The method of claim 20, wherein the composition is administered directly to the bronchia, nasal cavity, sinuses, mouth, larynx, trachea or carina.

22. The method of claim 21, wherein the composition is administered into at least one lung by direct administration to the carina, whereby the composition is transmitted to the main bronchi of at least one lung of the equine.

23. The method of claim 1, wherein the composition is administered to the equine through an endoscopic biopsy channel.

24. The method of claim 1, wherein the composition is administered to the equine by use of a nebulizer.

25. The method of claim 1, further comprising administering to the equine at least one of a platelet trigger or a diuretic.

26. The method of claim 25, wherein the platelet trigger or diuretic is administered previously, subsequently, or substantially simultaneously to the administration of the platelet enriched plasma.

27. The method of claim 25 or 26, wherein the composition comprises at least one of the platelet trigger or the diuretic.

28. The method of claim 25 or 26, wherein the administration of platelet enriched plasma and platelet trigger results in the release of at least one growth factor by platelet alpha granules.

29. The method of claim 28, wherein the at least one growth factor is selected from the group consisting of transforming growth factor beta (TGFbeta), vascular endothelial growth factor (VEGF), platelet-derived growth factor (PDGF), epidermal growth factor (EGF) and epithelial growth factor (EDF).

30. The method of claim 29, wherein the growth factor is TGFbeta.

31. The method of claim 25 or 26, wherein the diuretic is furosemide.

32. A method of treating exercise induced pulmonary hemorrhage in an equine comprising administering to the lung of the equine, a composition comprising autologous platelet enriched plasma, wherein the composition is infused at the level of the carina such that it is distributed to the main bronchi of at least one lung of the equine, thereby treating exercise induced pulmonary hemorrhage.

* * * * *